United States Patent
Rotter

(10) Patent No.: US 6,681,974 B2
(45) Date of Patent: Jan. 27, 2004

(54) FANNY PACK WITH INFLATABLE LUMBAR SUPPORT

(76) Inventor: Leah Rotter, 9155 Hillsboro Dr., Los Angeles, CA (US) 90034

(*) Notice: Subject to any disclaimer, the term of this patent is extended or adjusted under 35 U.S.C. 154(b) by 92 days.

(21) Appl. No.: 09/996,302

(22) Filed: Nov. 21, 2001

(65) Prior Publication Data
US 2003/0094474 A1 May 22, 2003

(51) Int. Cl.⁷ .................................. A45C 1/04
(52) U.S. Cl. ............... 224/662; 224/680; 224/681; 224/682; 128/876; 602/19
(58) Field of Search .................. 224/662, 680, 224/681, 682, 683, 907, 642, 644; 602/19; 128/876

(56) References Cited

U.S. PATENT DOCUMENTS

| | | | |
|---|---|---|---|
| 3,679,108 A * | 7/1972 | Ingram | 224/644 |
| 4,135,503 A * | 1/1979 | Romano | 602/13 |
| 4,552,135 A * | 11/1985 | Racz et al. | 602/13 |
| 4,993,409 A * | 2/1991 | Grim | 602/19 |
| 5,062,414 A * | 11/1991 | Grim | 602/19 |
| 5,195,948 A * | 3/1993 | Hill et al. | 602/19 |
| 5,205,814 A * | 4/1993 | Lundrigan et al. | 602/19 |
| 5,228,609 A * | 7/1993 | Gregory | 224/617 |
| 5,547,461 A * | 8/1996 | Levis | 602/19 |
| 5,645,080 A * | 7/1997 | Toso | 128/876 |
| 6,331,170 B1 * | 12/2001 | Ordway | 602/19 |
| 6,471,105 B1 * | 10/2002 | Ammerman et al. | 224/625 |

* cited by examiner

Primary Examiner—Stephen K. Cronin
(74) Attorney, Agent, or Firm—Natan Epstein

(57) ABSTRACT

A fanny pack of the type worn around a person's waist as a carrying bag has an inflatable air bladder and a hand operated air pump for inflating the air bladder to provide a lumbar support when the fanny pack is worn over the lower back of a seated person.

30 Claims, 3 Drawing Sheets

FANNY PACK WITH INFLATABLE LUMBAR SUPPORT

BACKGROUND OF THE INVENTION

1. Field of the Invention

This invention relates to a carrying bag worn on a belt around a user's waist, the bag containing an inflatable bladder serving as a lumbar support when the bag is worn against the lower back by a seated user.

2. State of the Prior Art

So-called fanny packs consist of a zippered pouch worn on a belt either over the belly or the back side (fanny) of the user's person. Fanny packs are popular as they serve the function of a handbag or purse without tying up the user's hands, and are also more secure against loss or theft by snatching.

Lumbar supports serve to provide support to the normally concave portion of the spinal column along the lower back when in a seated position. It is easy for the lower back to be pushed outwardly in a sitting position, which is undesirable for comfort and health. The benefits of lumbar supports have been widely recognized and many seats are now equipped with them. Still, there remain many situations where additional lumbar support is needed. Presently, lumbar support pillows including inflatable pillows may be used for this purpose. However, the need to keep such pillows on hand is an inconvenience, such that the lumbar support may not be available when needed.

SUMMARY OF THE INVENTION

The aforementioned need is addressed by this invention which provides a combination fanny pack with inflatable lumbar support comprising a bag, a zippered opening into the bag, a belt for securing the bag to a person's lower back, an inflatable bladder in the bag; a hand operated air pump external to the bag, and an air hose passing through an opening into the bag and connecting the pump for delivering pressurized air to the bladder. The combination fanny pack may also have a pump holder on the bag or the belt, such as a pump pocket with a flap for securing the pump in the pocket when the pump is not in use. Preferably, the pump holder is exterior to the bag.

The bladder has a width, a height and a thickness dimension, and the bladder is inflatable by pressurized air from the pump primarily for increasing its thickness dimension. The combination also has an air valve operable to a closed condition to keep the bladder in an inflated state and operable to an open condition for releasing air from or admitting air into the bag. A partition in the bag may be provided for substantially containing the bladder against an interior surface of the bag thereby to clear a portion of the bag interior for other bag contents. The partition may be a mesh or net supported within the bag, selected to be expandable with inflation of the air bladder.

The hand operated air pump may include a rubber bulb connected to the air hose and a valve associated with the rubber bulb operable for releasing or holding air in the bag. One or more additional pockets may be provided on the bag and or the belt for additional carrying capacity. In a preferred form of the invention the bag is made primarily of cloth such as a ballistic nylon fabric.

More particularly, the bag has a rear wall, a front wall joined to the rear wall at opposite sides of the bag, a top and a bottom, and a partition in the bag for supporting the bladder against the rear wall. The partition may extend between opposite sides of the bag. The air hose opening may be defined between the front wall and the rear wall on one of the opposite sides of the bag. It is also preferred that the air hose slides freely through the hose opening relative to the bag.

These and other features, improvements and advantages of the present invention will be better understood from the following detailed description of the preferred embodiments taken in conjunction with the accompanying drawings.

DETAILED DESCRIPTION OF THE PREFERRED EMBODIMENT

Figure 1:
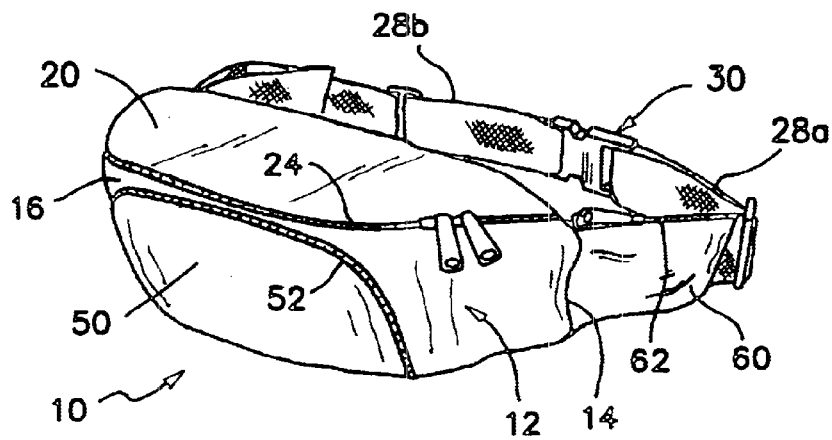
FIG. 1 is a front side perspective view of the fanny pack of this invention.

With reference to the accompanying drawings wherein like elements are designated by like numerals, the combination fanny pack/lumbar support of the invention is generally designated by the numeral 10. The fanny pack 10 includes a bag 12 of generally elongated shape having a front panel 16 and a rear panel 18 joined at two opposite side seams 14, a bag bottom 19 and a top cover 20 attached to the rear wall 18 along top edge 22. The front edge of the top cover is releasably secured to the front wall 16 by a fastener such as zipper 24. The top cover 20 hinges along top edge 22 and when lifted away from the front wall 16 defines a reclosable opening 24 into the bag interior 26.

A belt 28 has two belt segments 28a, 28b each attached to a corresponding one of the bag's opposite sides 14. A snap buckle or equivalent fastener 30 is provided for releasably fastening the belt 28 around a person's waist, with the bag 12 positioned either over the person's lower back or over the person's abdomen.

Figure 4:
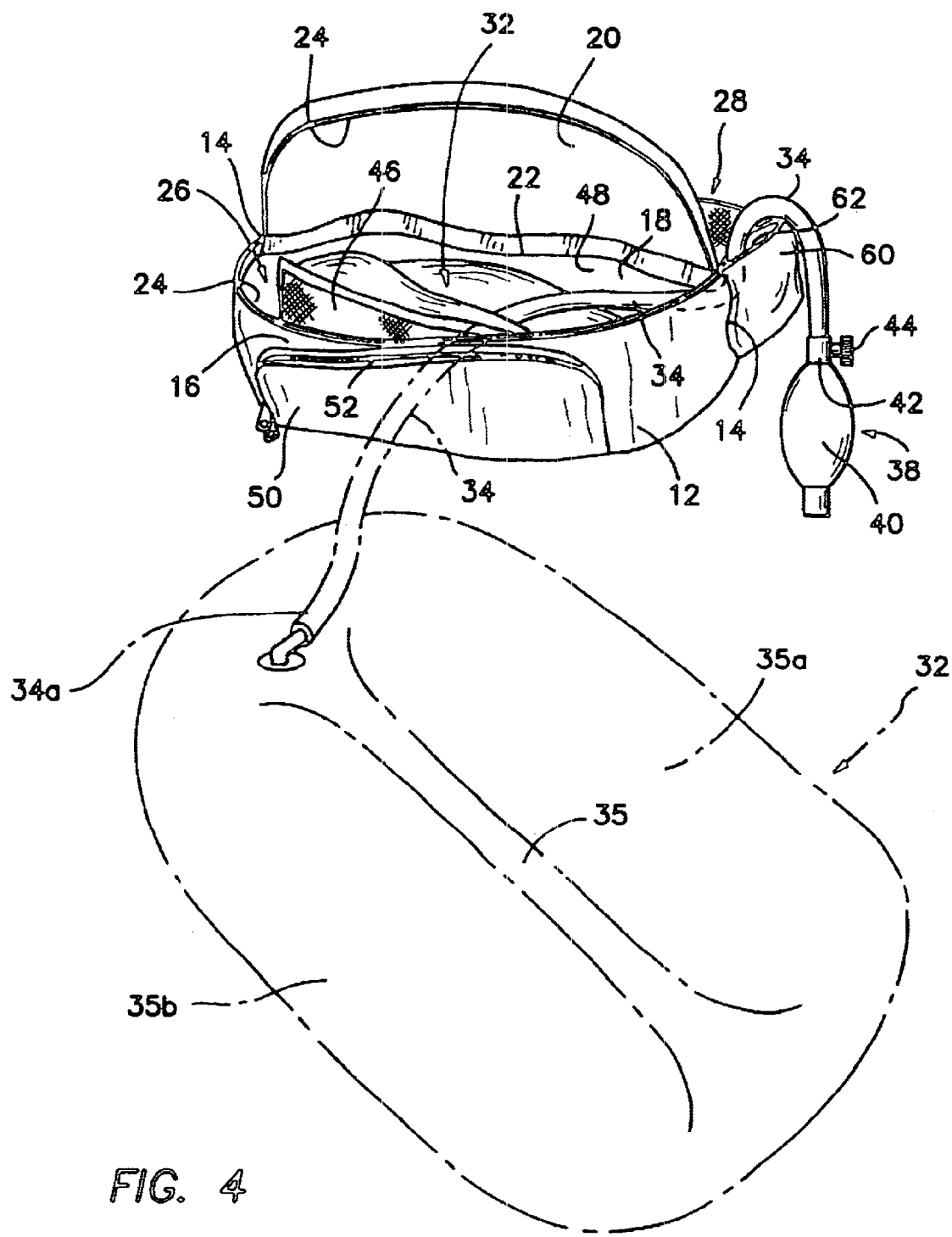
FIG. 4 shows the fanny pack with its top cover open, the air bladder shown deflated and the rubber bulb removed from the pump storage pocket for use and suggesting how the air tube passes into the pack interior through an opening in a corner seam of the pack; including a phantom view of the air bladder removed from the pack in an inflated condition for purposes of illustration.

An inflatable bladder 32 is contained in bag 12 as shown in FIG. 4. an air hose such as a length of flexible rubber tubing 34 passes through an opening in one side seam 14 of the bag between the rear bag interior 26 to the exterior of the bag 12, or any other conveniently positioned opening of small size sufficient to pass the diameter of the air tube. The interior end 34a of the air tube 34 is connected to the air bladder 32 as shown in phantom lining in FIG. 4. The exterior end 34b of the air tube 34 is connected to a hand operated air pump 38 external to said bag 12 for delivering pressurized air to the air bladder. The hose opening is defined between front wall 16 and rear wall 18 on one opposite side 14 of the bag, as indicated by numeral 70 in FIG. 6, preferably so that the air hose 34 slides freely through the hose opening relative to the bag so that a greater or lesser portion of the air hose may be slipped into or out of the bag interior 26 as needed by the user while actuating the air pump.

The air bladder 32 is preferably of generally rectangular shape with a width, a height and a thickness dimension, and is designed so that the bladder is inflatable by pressurized air from said pump primarily for increasing the thickness dimension. When deflated, the bladder collapses to a generally flat rectangular shape which can be folded as needed to fit the bladder within the bag interior 26. The length dimension of the bladder is preferably slightly undersized to the length of the bag interior between the bag sides 14. The width dimension of the bladder may be greater than the height of the bag interior between the bag bottom 19 and the top cover 20, the bladder being folded along its length so as to fit in the bag 12. When so folded the bag 12 contains two thicknesses of the bladder 32 between the front 16 and rear 18 for better expansion of the bag by the bladder. The bladder can be made, for example, of two sheets of suitable plastic material sealed around the edges, and preferably also joined along a middle area 35 to facilitate folding of the bladder and define two air chambers 35a, 35b open to each other at opposite ends of the bladder.

As seen in FIG. 4 of the drawings, in one form of the invention the partition or bladder restraint 46 has a free upper edge 46'asuch that a bladder space 47 is defined between the partition 46 and the rear wall 48 of the bag 12, and a carrying space 45 between the partition 46 and front wall 16. The partition 46 contains and restrains the deflated bladder 32 so as to leave clear the carrying space 45 while the bladder is deflated. Bladder 32 is contained in the bladder space 47, and is accessible through the access opening 24 defined by the open bag top 20. As indicated in the same FIG. 4 the bladder may be removable from the bladder space 47 and the bag interior 26 through the access opening 24 from the folded solid lined condition to the phantom lined condition in FIG. 4.

The preferred air pump 38 is a rubber bulb 40 equipped with an air valve 42 which is operable by turning a valve control 44 between a closed condition for holding compresssed air to keep the bladder 32 in an inflated state, and an open condition for inflating the bladder while pumping the bulb 40 or releasing compressed air for deflating the bladder. Suitable rubber bulb air pumps are commercially available and are used, for example, for inflating pressure cuffs in clinical blood pressure manometers. A pump holder or storage pocket 60 exterior to the bag 12 is attached to or formed integrally with the belt 28 adjacently to one side 14 of bag 12. The pump storage pocket 60 has a zippered opening 62 for securing the rubber bulb in pocket 60 when the bulb 40 is not in use.

When inflated by repeated manual compression of the bulb 40, the air bladder 32 expands primarily in thickness to spread apart the front wall 16 from the rear wall 18. That is, the front 16 of the fanny pack 10 expands away from the body of the person wearing the fanny pack. The degree of expansion of the bag 12 is readily controllable by the user by inflating the bladder to the desired volume and degree of firmness. Over-inflation is easily corrected by briefly opening the valve control 44 to release the necessary amount of air from the bladder 32.

The bag 12 serves the dual functions of containing and supporting the inflated air bladder 32 in proper position for lumbar support and of serving as a carrying bag or pouch when the bladder is deflated. A partition in the form of a mesh or net 46 is sewn or otherwise secured between the opposite bag sides 14 for substantially containing the bladder 32 against an interior surface of the bag, preferably against the interior surface 48 of the rear wall 18, so as to clear interior space in the bag for such articles as the user of the fanny pack 10 may wish to carry in the bag 12. The partition is preferably made of an elastic material which is expandable or stretchable with inflation of the air bladder.

Figure 2:
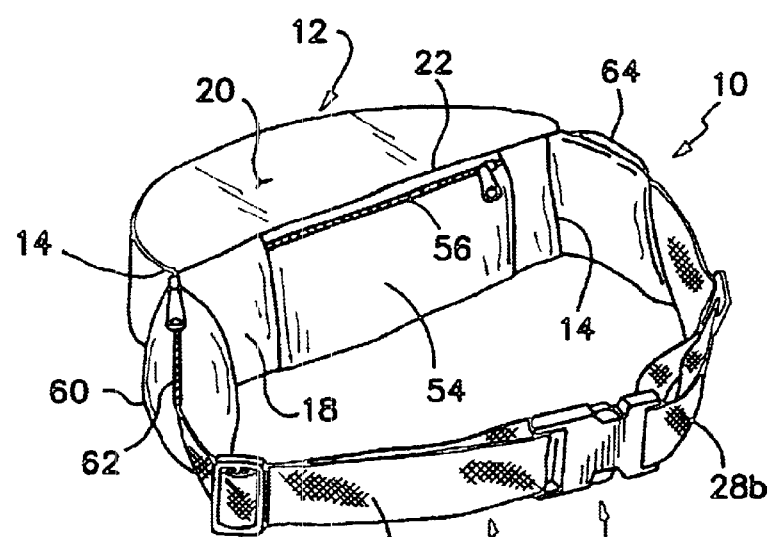
FIG. 2 is a rear side perspective view of the fanny pack of FIG. 1.
Figure 3:
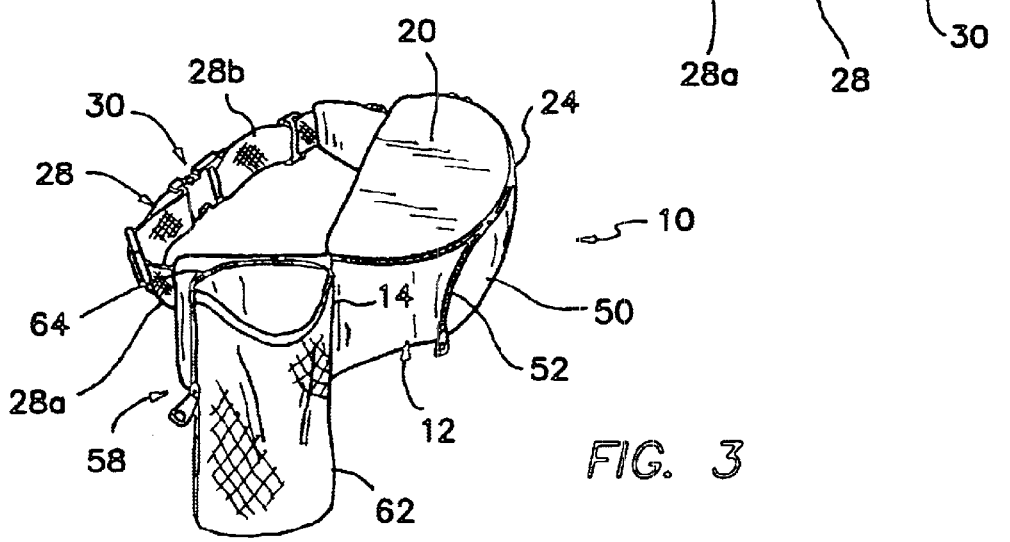
FIG. 3 is a top left side perspective view of the fanny pack of FIG. 1.

Additional pockets may be provided on the exterior of the bag 12 or on the belt 28. For example, as shown in FIGS. 1, 3 and 4, a front pocket 50 may be sewn onto the exterior of the front wall 16 and provided with a zippered closure 52. A rear pocket 54 may be sewn onto the rear wall 18 as shown in FIG. 2, with a zippered closure 56. Optionally, a water bottle holder 58 may be attached to belt 28 adjacent to the side 14 opposite to the pump pocket 60. The bottle holder may include a mesh bag 62 sized to receive the bottom of a bottle, and a zippered pouch 64 for containing the mesh bag in folded condition when not needed for holding a bottle. The bag 12 and exterior pockets may be made of suitable cloth, such as so called "ballistic" nylon fabric conventionally used in luggage generally and fanny packs in particular.

Figure 5:
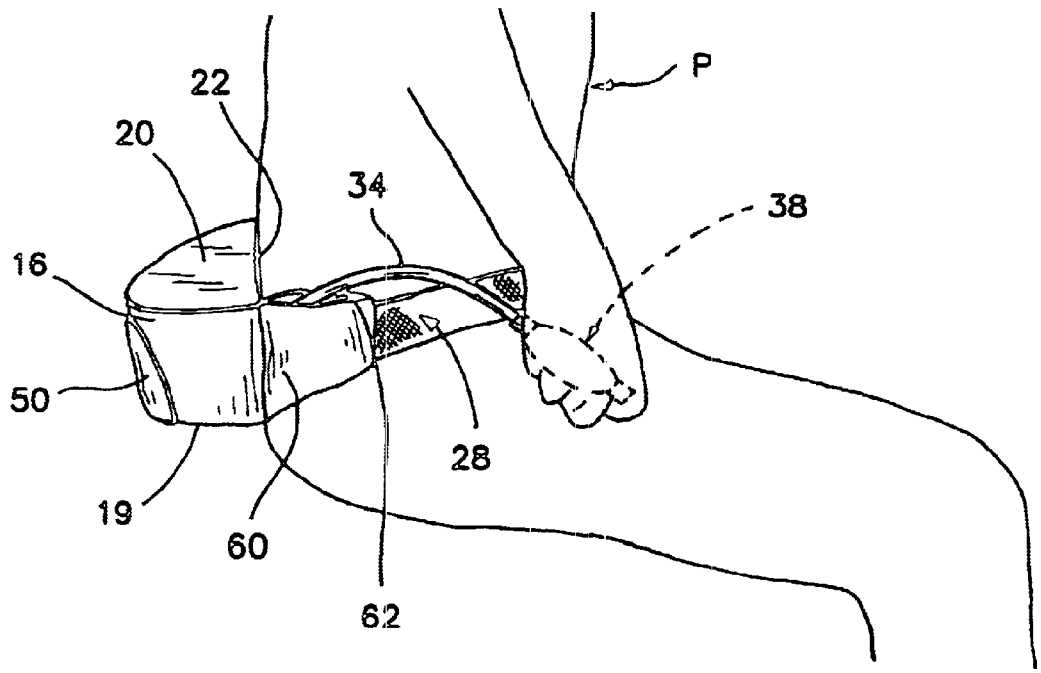
FIG. 5 is a partial side view of a person's body in seated position wearing the fanny pack for lumbar support and holding the rubber bulb in one hand for inflating the air bladder in the fanny pack.

FIG. 5 shows the fanny pack 10 worn on the person of a user P for use as a lumbar support. For this purpose the belt 28 is worn and fastened around the waist of the user with the bag 12 positioned over the lower back or lumbar region of the user's backside. When the fanny pack 10 is to be used as a lumbar support it is best to empty the bag 12 of any articles being carried in the interest of comfort and to avoid possible damage to the bladder 32. The user reclines against a back support of the seat with the bag 12 between the user and the back support. The bladder is then inflated by user P by appropriate operation of the hand pump 38 so as to achieve a desired degree of inflation of the air bladder 32 inside the bag 12 for comfortable lumbar support. When no longer needed for lumbar support, the bladder is deflated by release of air through valve 42, and articles may be replaced in the bag 12 for carrying. The air tube 34 is of sufficient length to permit the user P to hold the bulb comfortably to one side of his or her person while inflating or deflating the air bladder 32 against his or her backside.

Figure 6:
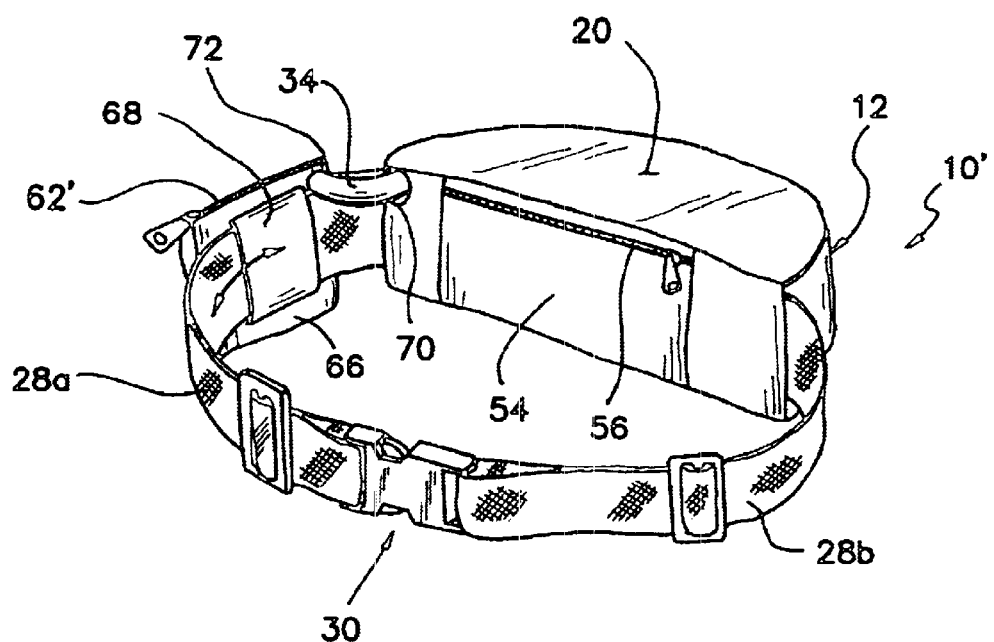
FIG. 6 is a rear top perspective view of a modified form of the fanny pack provided with a separate pouch slidable along the belt of the fanny pack for storing the air pump bulb.

FIG. 6 depicts an alternate fanny pack 10' wherein the pump storage pocket 60 is replaced with a separate pouch 66 which is supported on a belt loop 68 for sliding movement along the belt segment 28a, and the bottle carrier 64 has been removed. The air tube 34 passes out of the bag 12 through an opening 70, or optionally, through the zippered top opening 62', and enters the storage pouch through an opening 72. Both openings 70, 72 are preferably sized to allow the air tube to slide freely therethrough.

While a particular embodiment of the invention has been shown and described for purposes of clarity and illustration, it must be understood that many changes, substitutions and modifications to the described embodiment will be apparent to those having only ordinary skill in the art without thereby departing from the scope of the invention as defined in the following claims.

What is claimed is:

1. A combination fanny pack with inflatable lumbar support comprising:

a bag having a bag interior defined between a rear wall, a front wall joined to said rear wall at opposite sides of said bag, a bag bottom, and a top releaseably fastened for defining a recloseable access opening into said bag interior, a belt for securing said bag to a person's waist, a bladder in said bag interior, a pump external to said bag operable for inflating said bladder, and an expandable restraint in said bag interior arranged for substantially containing said bladder in a deflated condition against an interior surface of said bag so as to define a carrying space in said bag interior for carrying any articles placed therein by a user of the fanny pack, said bladder being inflatable against said expandable restraint by said pump for substantially filling said bag interior including said carrying space.

2. The combination of claim 1 wherein said bladder has a width, a height and a thickness dimension, and said bladder is inflatable by pressurized air from said pump primarily for increasing said thickness dimension.

3. The combination of claim 1 further comprising an air valve operable to a closed condition to keep said bladder in an inflated state or operable to an open condition for releasing air from or admitting air into said bladder.

4. The combination of claim 1 further comprising one or more additional pockets on said bag or said belt.

5. The combination of claim 1 wherein said bag is made primarily of cloth.

6. The combination of claim 1 wherein said partition extends between said opposite sides of said bag.

7. The combination of claim 1 wherein said partition is an elastic mesh.

8. The combination fanny pack of claim 1 wherein said expandable restraint is arranged for containing said bladder against one said wall and said carrying space is defined between said expandable restraint and another said wall.

9. The combination fanny pack of claim 1 wherein said restraint is arranged for containing said bladder against said rear wall and wherein said carrying space is defined between said restraint and said front wall.

10. The combination fanny pack of claim 1 wherein said restraint is arranged for containing said bladder against said rear wall and defining said carrying space between said restraint and said front wall and wherein said bag top is hinged to said rear wall and zippered to said front wall to provide said recloseable access.

11. The combination fanny pack of claim 1 wherein said expandable restraint is an elastic mesh.

12. The combination fanny pack of claim 1 said belt is attached to said opposite sides of said bag.

13. The combination fanny pack of claim 1 wherein said expandable restraint extends between said opposite sides of said bag.

14. The combination fanny pack of claim 1 wherein said top is hinged to said rear wall and zippered to said front wall to provide said recloseable access.

15. The combination of claim 1 further comprising an air hose passing through an opening into said bag and connecting said pump for delivering pressurized air to said bladder.

16. The combination of claim 15 wherein said hose opening is defined between said front wall and said rear wall on one of said opposite sides of said bag.

17. The combination of claim 15 wherein said hose slides freely through said hose opening relative to said bag.

18. The combination of claim 15 wherein said pump comprises a rubber bulb connected to said air hose.

19. The combination of claim 18 wherein said rubber bulb has a valve operable for releasing air from or holding air in said bladder.

20. The combination of claim 1 further comprising a pump holder attached to said bag or said belt for storing said pump when not in use.

21. The combination of claim 20 wherein said pump holder is exterior to said bag.

22. The combination of claim 20 wherein said pump holder comprises a pump pocket.

23. The combination fanny pack of claim 1 wherein said bladder and said carrying space are both accessible through said recloseable access opening.

24. The combination fanny pack of claim 23 wherein said bag is primarily made of cloth.

25. The combination fanny pack of claim 23 wherein said partition is an elastic mesh.

26. The combination fanny pack of claim 23 wherein said bladder and said carrying space are both accessible through said top.

27. The combination fanny pack of claim 23 wherein said bladder is accessible interior through said top of said bag.

28. The combination fanny pack of claim 23 wherein said bladder is removable from said bag interior through said top of said bag.

29. The combination fanny pack of claim 23 wherein said partition has a free upper edge such that said bag interior including a bladder containing space between said partition and said rear wall is accessible in an open condition of said top.

30. A combination fanny pack with inflatable lumbar support comprising:

a bag having a bag interior defined between a rear wall, a front wall joined to said rear wall at opposite sides of said bag, a bottom, and a top hinged to said rear wall and zippered to said front wall to provide access into said bag interior, a belt fastened to said opposite sides for securing said bag to a person's waist, a bladder in said bag interior, a pump external to said bag operable for inflating said bladder, an elastic partition extending between said opposite ends for substantially containing said bladder in a deflated condition against said rear wall so as to define a carrying space in said bag interior between said restraint and said front wall for carrying any articles placed therein by a user of the fanny pack, said bladder being inflatable against said expandable restraint by said pump for substantially filling said bag interior including said carrying space.

* * * * *